United States Patent [19]

Oshiro et al.

[11] Patent Number: 5,656,633

[45] Date of Patent: Aug. 12, 1997

[54] CARBOSTYRIL DERIVATIVES AND PHARMACEUTICAL COMPOSITIONS CONTAINING THE SAME FOR USE AS A DISTURBANCE-OF-CONSCIOUSNESS IMPROVING AGENT, CENTRAL NERVOUS SYSTEM STIMULANT OR SIGMA RECEPTOR AGONIST

[75] Inventors: Yasuo Oshiro, Tokushima; Tatsuyoshi Tanaka, Tokushima-ken; Tetsuro Kikuchi, Tokushima; Katsura Tottori, Tokushima-ken, all of Japan

[73] Assignee: Otsuka Pharmaceutical Co., Ltd., Tokyo, Japan

[21] Appl. No.: 465,579

[22] Filed: Jun. 5, 1995

Related U.S. Application Data

[63] Continuation of Ser. No. 82,522, Jun. 25, 1993, abandoned, which is a continuation of Ser. No. 878,515, May 5, 1992, abandoned.

[30] Foreign Application Priority Data

May 8, 1991 [JP] Japan .................... 3-102391

[51] Int. Cl.⁶ .................... A61K 31/505; C07D 401/06
[52] U.S. Cl. .................... 514/253; 544/363
[58] Field of Search ................ 544/363; 514/253

[56] References Cited

U.S. PATENT DOCUMENTS

| | | | |
|---|---|---|---|
| 3,629,266 | 12/1971 | Havera | 514/253 |
| 3,682,920 | 8/1972 | Havera | 514/253 |
| 3,699,092 | 10/1972 | Weaver et al. | 514/253 |

FOREIGN PATENT DOCUMENTS

| | | |
|---|---|---|
| 0226441 | 6/1987 | European Pat. Off. . |
| 0236140 | 9/1987 | European Pat. Off. . |
| 0283310 | 9/1988 | European Pat. Off. . |
| 2915250 | 10/1980 | Germany . |
| 83781 | 6/1980 | Japan . |
| 264773 | 8/1980 | Japan . |
| 49359 | 5/1981 | Japan . |
| 4974 | 1/1982 | Japan . |
| 146872 | 6/1988 | Japan . |
| 272524 | 10/1989 | Japan . |
| 279868 | 11/1989 | Japan . |
| 102568 | 10/1990 | Japan . |
| 2023594 | 1/1980 | United Kingdom . |
| WO9109594 | 7/1991 | WIPO . |

OTHER PUBLICATIONS

Gewirtz et al. Neuropsychopharmacology, 1994, pp. 37–40.
Havera et al, Journal of Med. Chem. vol. 12, p. 580 (1964).
Chemical Abstracts, vol. 68: 2796s.
Chemical Abstracts, vol. 96: 31489c.
Chemical Abstracts, vol. 58: 2435.
Chemical Abstracts, vol. 59: 1002.
Chemical Abstracts, vol. 55: 15750.
Chemical Abstracts, vol. 56: 14885.
Chemical Abstracts, vol. 59: 9971.
Journal of Medicinal Chemistry, Vo. 12, pp. 580–583.
Yakugaku Zasshi 92 (6), pp. 772–774, 1972.
Chemical Abstracts, vol. 77: 114211q.
Chemical Abstracts, vol. 112: 55541p.
Chemical Abstracts, vol. 58: 13945.
Chemical and Pharmaceutical Bulletin, vol. 9, pp. 970–975, 1961.

*Primary Examiner*—Matthew V. Grumbling
*Assistant Examiner*—Sabiha N. Qazi
*Attorney, Agent, or Firm*—Sughrue, Mion, Zinn, Macpeak & Seas

[57] ABSTRACT

Disclosed is carbostyril derivatives of the general formula

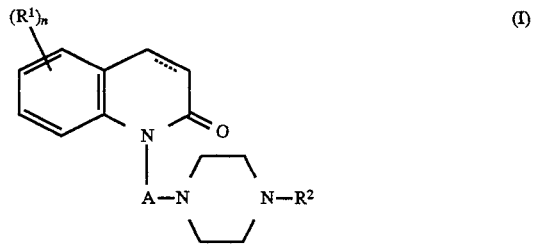

wherein $R^1$ is a halogen, a hydroxyl, lower alkoxy, lower alkyl, lower alkenyloxy, amino, lower-alkanoyl amino or lower alkylthio group, $R^2$ is a phenyl group which may optionally have one or two substituents, A is a lower alkylene group, and n is an integer of 1 or 2 and wherein the carbon-carbon bond between the positions 3 and 4 of the carbostyril skeleton may be a single bond or a double bond, and salts thereof, and pharmaceutical compositions containing the same for use as a disturbance-of-consciousness improving agent, central nervous system stimulant or sigma receptor agonist.

13 Claims, No Drawings

CARBOSTYRIL DERIVATIVES AND PHARMACEUTICAL COMPOSITIONS CONTAINING THE SAME FOR USE AS A DISTURBANCE-OF-CONSCIOUSNESS IMPROVING AGENT, CENTRAL NERVOUS SYSTEM STIMULANT OR SIGMA RECEPTOR AGONIST

This is a continuation of application Ser. No. 08/082,522 filed Jun. 25, 1993, now abandoned; which in turn is a continuation of application Ser. No. 07/878,515 filed May 5, 1992 (now abandoned).

The present invention relates to novel carbostyril derivatives and pharmaceutical compositions containing the same for use as a disturbance-of-consciousness improving agent, central nervous system stimulant or sigma receptor agonist.

It is an object of the invention to provide carbostyril derivatives of value as a disturbance-of-consciousness improving agent, central nervous system stimulant or sigma receptor agonist.

Another object of the invention is to provide a pharmaceutical composition for use as a disturbance-of-consciousness improving agent.

A further object of the invention is to provide a pharmaceutical composition for use as a central nervous system stimulant.

A still further object of the invention is to provide a pharmaceutical composition for use as a sigma receptor agonist.

Other features of the invention will become apparent as the following description proceeds.

The invention provides carbostyril derivatives of the general formula

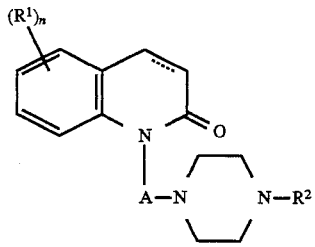

wherein $R^1$ is a halogen, a hydroxyl, lower alkoxy, lower alkyl, lower alkenyloxy, amino, lower alkanoyl amino or lower alkylthio group, $R^2$ is a phenyl group which may optionally have one or two substituents each independently selected from the group consisting of halogen, lower alkoxy, lower alkyl, nitro, amino, lower alkanoylamino, hydroxyl, cyano, phenyl-lower alkoxy and halo-lower alkyl, A is a lower alkylene group, and n is an integer of 1 or 2 and wherein the carbon-carbon bond between the positions 3 and 4 of the carbostyril skeleton may be a single bond or a double bond, and salts thereof.

The compounds of this invention have central nervous system stimulant and disturbance-of-consciousness improving activities and are useful as therapeutic agents for head trauma, cerebral hemorrhage, cerebral infarction, subarachnoid hemorrhage, drug poisoning, anoxia, accidents due to shortage of oxygen, disturbance of consciousness following surgical operation of the brain and coronary artery by pass surgery, and sequelae thereof such as mental retardation, decreased attention, speech disturbance, cognitive disorder, behavioral disorder, decreased volition, emotional disturbance and the like and, further, as agents for ameliorating symptoms of senile dementia, such as depressed state, delirium, speech disturbance, behavioral disorder, decreased attention and age-associated memory impairment. Furthermore, the compounds of this invention have sigma receptor agonistic activity and are useful as therapeutic agents for depression, anxiety neurosis, psychosomatic disorder, other stress-induced mental disorders, anorexia nervosa, hypopituitarism, hyperprolactinemia, vascular dementia, hyperkinetic syndrome, dementia/amnesia, parkinsonism and the like. They can be used also as antidepressants, antianxiety agents, therapeutic agents for psychosomatic disorder and parkinsonism, and so forth.

A special feature of the compounds of the invention is that even when they are orally administered, they show central nervous system activating, disturbance-of-consciousness improving and sigma receptor agonistic activities.

The groups represented by the symbols appearing in the above general formula (1) are described below more specifically.

The halogen atom is, for example, a fluorine, chlorine, bromine or iodine atom.

The lower alkoxy group includes straight or branched alkoxy groups containing 1 to 6 carbon atoms, such as methoxy, ethoxy, propoxy, isopropoxy, butoxy, tert-butoxy, pentyloxy and hexyloxy.

The lower alkyl group includes straight or branched alkyl groups containing 1 to 6 carbon atoms, such as methyl, ethyl, propyl, isopropyl, butyl, tert-butyl, pentyl and hexyl.

The lower alkenyloxy group includes straight or branched alkenyloxy groups containing 2 to 6 carbon atoms, such as vinyloxy, allyloxy, 2-butenyloxy, 3-butenyloxy, 1-methylallyloxy, 2-pentenyloxy and 2-hexenyloxy.

The lower alkanoylamino group includes straight or branched alkanoylamino groups containing 1 to 6 carbon atoms, such as formylamino, acetylamino, propionylamino, butyrylamino, isobutyrylamino, pentanoylamino, tert-butylcarbonylamino and hexanoylamino.

The lower alkylthio group includes straight or branched alkylthio groups containing 1 to 6 carbon atoms, such as methylthio, ethylthio, propylthio, isopropylthio, butylthio, tert-butylthio, pentylthio and hexylthio.

The phenyl-lower alkoxy group includes phenylalkoxy groups in which the alkoxy moiety is a straight or branched alkoxy group containing 1 to 6 carbon atoms, for example, benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy and 2-methyl-3-phenylpropoxy.

The halo-lower alkyl group includes straight or branched alkyl groups containing 1 to 6 carbon atoms and having 1 to 3 halogen atoms, for example chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2-trichloroethyl, 3-fluoropropyl, 3,3,3-trichloropropyl, 4-chlorobutyl, 5-chloropentyl, 6-chlorohexyl and 3-chloro-2-methylpropyl.

The phenyl group which may optionally have one or two substituents each independently selected from the group consisting of halogen, lower alkoxy, lower alkyl, nitro, amino, lower alkanoylamino, hydroxyl, cyano, phenyl-lower alkoxy and halo-lower alkyl includes phenyl and mono- and di-substituted phenyl groups in which each substituent on the benzene ring is independently selected from the group consisting of halogen, straight or branched alkoxy containing 1 to 6 carbon atoms, straight or branched alkyl containing 1 to 6 carbon atoms, nitro, amino, straight or branched alkanoylamino containing 1 to 6 carbon atoms, hydroxyl, cyano, phenylalkoxy in which the alkoxy moiety is straight or branched alkoxy containing 1 to 6 carbon atoms, and straight or branched alkyl containing 1 to 6 carbon atom and having 1 to 3 halogen atoms, such as, for example, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 2-methoxy-3-chlorophenyl, 2-methylphenyl, 3-methylphenyl, 4-methylphenyl, 2-ethylphenyl, 3-ethylphenyl, 4-ethylpenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3-chloro-4-methylphenyl, 2-trifluoromethylphenyl, 3-trifluoromethylphenyl, 4-trifluoromethylphenyl, 2-chloromethylphenyl, 3-(2-bromoethyl)phenyl, 4-(3,3,3-trichloropropyl)phenyl, 2-(4-chlorobutyl)phenyl, 3-(5-chloropentyl)phenyl, 4-(6-chlorohexyl)phenyl, 2-nitrophenyl, 3-nitrophenyl, 4-nitrophenyl, 3,4-dinitrophenyl, 3,4,5-trinitrophenyl, 2-aminophenyl, 3-aminophenyl, 4-aminophenyl, 2-formylaminophenyl, 3-acetylaminophenyl, 2-propionylaminophenyl, 4-butyrylaminophenyl, 3-pentanoylaminophenyl, 4-hexanoylaminophenyl, 2-acetylamino-4-methylphenyl, 4-acetylamino-3-methoxyphenyl, 2-hydroxyphenyl, 3-hydroxyphenyl, 4-hydroxyphenyl, 2,3-dihydroxyphenyl, 2,4,6-trihydroxyphenyl, 2-cyanophenyl, 3-cyanophenyl, 4-cyanophenyl, 3,4-dicyanophenyl, 2-benzyloxyphenyl, 3-(2-phenylethoxy)phenyl, 4-(1-phenylethoxy)phenyl, 2-(3-phenylpropoxy)phenyl, 3-(4-phenylbutoxy)phenyl, 4-(5-phenylpentyloxy)phenyl and 2-(6-phenylhexyloxy)phenyl.

The lower alkylene group includes straight or branched alkylene groups containing 1 to 6 carbon atoms, such as methylene, ethylene, trimethylene, 2-methyltrimethylene, 1-methyltrimethylene, tetramethylene, pentamethylene, hexamethylene, 2-ethylethylene and 2,2-dimethyltrimethylene.

The compounds of this invention can be produced by several methods. In a preferred embodiment, they can be produced by the following process (process 1):

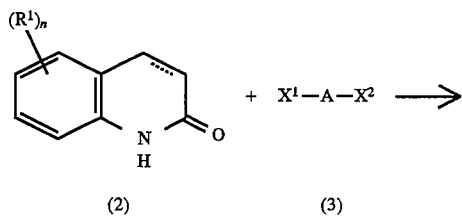

(2)  (3)

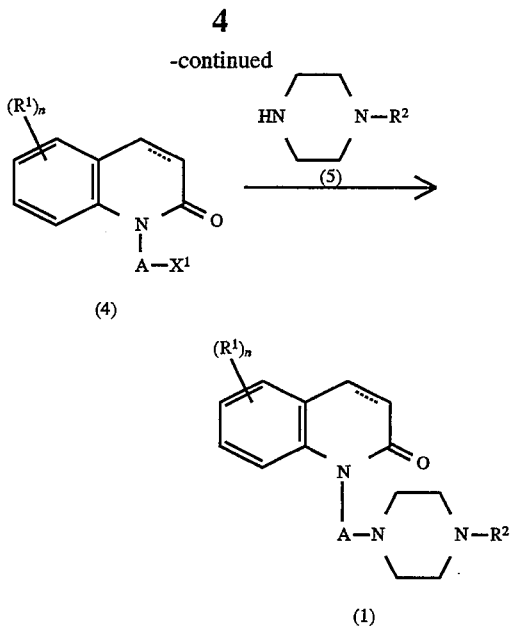

In the above reaction formula $R^1$, $R^2$, A, n and the carbon-carbon bond between the positions 3 and 4 of the carbostytil skeleton are as defined above, and $X^1$ and $X^2$ each is a halogen atom.

In the above process 1, the compound of general formula (2) can readily be reacted with the compound of general formula (3) in an appropriate inert solvent in the presence of a hydrogen halide acceptor. The quantity ratio between the compound of general formula (2) and the compound of general formula (3) is not critical but may suitably be selected within a wide range. Generally, however, the latter is used preferably in an amount of not less than 1 mole, more preferably 1 to 3 moles, per mole of the former. The hydrogen halide acceptor is, for example, an alkali metal such as sodium or potassium, an alkali metal amide such as sodium amide or potassium amide, or a sodium hydride. As the inert solvent, there may be mentioned, among others, aromatic hydrocarbons such as benzene, toluene and xylene, ethers such as tetrahydrofuran, dioxane and ethylene glycol dimethyl ether, dimethyl sulfoxide, dimethylformamide and hexamethylphosphoric triamide. Said reaction is carried out generally at 0° to 150° C., preferably 0° to 100° C., and is generally complete in about 1 to about 12 hours. The compound of general formula (4) is thus obtained.

The reaction of the compound of general formula (4) with the compound of general formula (5) is carried out without using any solvent or in a conventional inert solvent at room temperature to 200° C., preferably 60° to 120° C., and is complete in about 1 to about 10 hours. Usable as the inert solvent are aromatic hydrocarbons such as mentioned above, ethers such as mentioned above, lower alcohols such as methanol, ethanol and isopropanol, acetonitrile, dimethylformamide, dimethyl sulfoxide and the like polar solvents. It is more advantageous to carry out the above reaction in the presence of a basic compound as a hydrogen halide acceptor. Said basic compound is, for example, potassium carbonate, sodium carbonate, sodium hydroxide, sodium hydrogen carbonate, sodium amide, sodium hydride, triethylamine, tripropylamine, pyridine, 1,8-diazabicyclo[5.4.0]undecene-7 (DBU), or the like organic base. The above reaction may be accelerated, as necessary, by adding an alkali metal iodide (e.g. potassium iodide, sodium iodide) as a reaction promoter. The quantity ratio between the compound of general formula (4) and the compound of general formula (5) to be subjected to the above reaction is not critical but, generally, the latter is used in an amount of 1 mole or in excess, preferably 1 to 5 moles, per mole of the former.

The compounds of this invention which are represented by the above general formula (1) can be produced also by the following process (process 2):

bons such as dichloromethane and chloroform. The lower alkanoic acid anhydride or lower alkanoyl halide is used at least in an equimolar amount, generally in an amount ranging from equimolar to large excess. Said reaction is advantageously carried out at room temperature to about 150° C. and is generally complete in about 0.5 to about 5 hours.

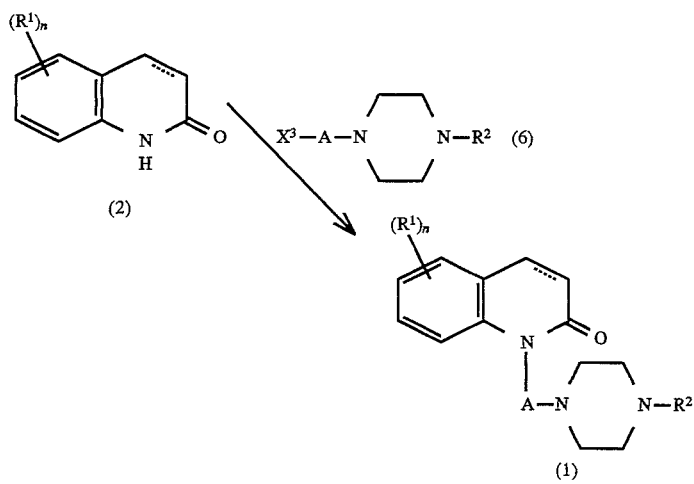

In the above reaction formula, $R^1$, $R^2$, A, n and the carbon-carbon bond between the positions of 3 and 4 of the carbostyril skeleton are as defined above and $X^3$ is a halogen atom.

In the above process 2, the reaction of the compound of general formula (2) with the compound of general formula (6) can be carried out in the same manner as mentioned above for the reaction of the compound of general formula (2) with the compound of general formula (3). The compound of general formula (6) can be readily prepared by reacting, for example, the above-mentioned compound of general formula (5) with the compound of general formula (3). The reaction between the compound of general formula (3) and the compound of general formula (5) can be carried out in the same manner as mentioned above for the reaction between the compound of general formula (4) and the compound of general formula (5).

Among the compounds of the invention which are represented by the above general formula (1), those compounds in which $R^1$ is a lower alkanoylamino group and those compounds in which $R^2$ is a phenyl group having at least one lower alkalnoylamino group as a substituent on the benzene ring can be produced by lower alkanoylating the corresponding compounds in which $R^1$ is an amino group and those in which $R^2$ is a phenyl group having at least one amino group as a substituent on the benzene ring, respectively.

The lower alkanoylation mentioned above is effected, for example, by reacting the starting compounds with a lower alkanoic acid anhydride without using any solvent or in an appropriate inert solvent, in the presence of a basic compound, or by reacting the starting compounds with a lower alkanoic acid anhydride or lower alkanoyl halide in an appropriate inert solvent. As the basic compound to be used, there may be mentioned organic bases such as pyridine, 4-dimethylaminopyridine and triethylamine and inorganic bases such as sodium carbonate and potassium carbonate. As the inert solvent, there may be mentioned, for example, acetic acid, pyridine, ethers such as dioxane, aromatic hydrocarbons such as benzene, and halogenated hydrocar- Among the compounds of the invention which are represented by the above general formula (1), those compounds in which $R^1$ is an amino group or those compounds in which $R^2$ is a phenyl group having at least one amino group as a substituent on the benzene ring can be produced by hydrolyzing the corresponding compounds in which $R^1$ is a lower alkanoylamino group and those in which $R^2$ is a phenyl group having at least one lower alkanoylamino group as a substituent on the benzene ring, respectively.

The above hydrolysis is carried out in an appropriate inert solvent or without using any solvent, in the presence of an acid. The solvent may be any of those conventional ones which do not adversely affect the reaction, including, for example, water, halogenated hydrocarbons such as dichloroethane and chloroform, lower alcohols such as methanol, ethanol and isopropanol, ketones such as acetone and methyl ethyl ketone, ethers such as dioxane, tetrahydrofuran, ethylene glycol monomethyl ether and ethylene glycol dimethyl ether, fatty acids such as formic acid, and mixed solvents composed of these. As the acid, there may be mentioned, for example, inorganic acids such as hydrochloric acid, sulfuric acid, hydrobromic acid, and organic acids such as formic acid, trifluoroacetic acid, acetic acid and aromatic sulfonic acids. The amount of the acid is not critical but may be selected within a wide range. Generally, however, it is used preferably in an amount of about 1 to about 10 moles per mole of each starting compound. Generally, said reaction progresses smoothly at room temperature to a temperature of about 200° C., preferably at room temperature to about 150° C., and is generally complete in about 0.5 to about 5 hours.

Among the compounds of the invention which are represented by the above general formula (1), those compounds in which $R^2$ is a phenyl group having at least one amino group as a substituent on the benzene ring can be produced by reducing the corresponding compounds in which $R^2$ is a phenyl group having at least one nitro group as a substituent on the benzene ring.

The above reduction reaction can be carried out, for example (1) by the catalytic reduction method using a catalyst in an appropriate solvent or (2) with a reducing agent such as a mixture of a metal or a metal salt with an acid or with an alkali metal hydroxide, a sulfide or an ammonium salt in an appropriate inert solvent.

In the case of catalytic reduction mentioned above under (1), the solvent to be used includes, among others, water, acetic acid, alcohols such as methanol, ethanol and isopropanol, hydrocarbons such as hexane and cyclohexane, ethers such as dioxane, tetrahydrofuran, diethyl ether and diethylene glycol dimethyl ether, esters such as ethyl acetate and methyl acetate, aprotic polar solvents such as N,N-dimethylformamide, and mixed solvents composed of these. The catalyst for catalytic reduction to be used is, for example, palladium, palladium black, palladium-carbon, platinum, platinum oxide, copper chromite, or Raney nickel. Preferably, said catalyst is used in an amount of about 0.02 to 1 part by weight per part of the starting compound. The reaction temperature is generally about −20° to about 150° C., preferably about 0° to about 100° C., and the hydrogen pressure is preferably about 1 to about 10 atmospheres. Said reaction is generally complete in about 0.5 to about 10 hours. An acid such as hydrochloric acid may be added to the reaction system for said reaction.

When the method mentioned above under (2) is used, the reducing agent to be used is, for example, a mixture of iron, zinc, tin or ferrous chloride and an inorganic acid such as hydrochloric acid or sulfuric acid or a mixture of iron, ferrous sulfate, zinc or tin and an alkali metal hydroxide such as sodium hydroxide, a sulfide such as ammonium sulfide, aqueous ammonia or an ammonium salt such as ammonium chloride. The inert solvent to be used is, for example, water, acetic acid, methanol, ethanol or dioxane. The conditions for the above reduction reaction may suitably be selected depending on the reducing agent employed. Thus, for instance, when reducing agent comprises stannous chloride and hydrochloric acid, the reaction is recommendably carried out at about 0° C. to room temperature for about 0.5 to about 10 hours. The reducing agent is used at least in an equimolar amount relative to the starting compound, generally in an amount of 1 to 5 moles per mole of the starting compound.

Among the compounds of the invention which are represented by the above general formula (1), those compounds in which the carbon-carbon bond between the positions 3 and 4 of the carbostyril skeleton is a double bond can be produced by dehydrogenating the corresponding compounds in which said bond is a single bond, in the per se conventional manner. Among the compounds of the invention which are represented by the above general formula (1), those compounds in which the carbon-carbon bond between the positions 3 and 4 of the carbostyril skeleton is a single bond can be produced also by subjecting the corresponding compounds in which said bond is a double bond to catalytic reduction in the per se conventional manner.

The compounds of general formula (1) which are to serve as active ingredients in accordance with the invention may readily-form salts with pharmacologically acceptable conventional acids. As such acids, there may be mentioned inorganic acids such as sulfuric acid, nitric acid, hydrochloric acid and hydrobromic acid, and organic acids such as acetic acid, p-toluenesulfonic acid, ethanesulfonic acid, oxalic acid, maleic acid, fumaric acid, citric acid, succinic acid and benzoic acid. These salts can also be used as active ingredient compounds of the present invention, just as the free compounds of general formula (1). The compounds of general formula (1) mentioned above include within the scope thereof all possible stereoisomers and optical isomers thereof. Such isomers can be used as active ingredient compounds as well.

The desired compounds obtained by the processes illustrated above by way of reaction formulas can be separated from the reaction systems by conventional means for separation and further purified. Useful as the means for separation and purification are, for example, distillation, recrystallization, column chromatography, ion exchange chromatography, gel chromatography, affinity chromatography, preparative thin layer chromatography, and solvent extraction.

The thus-obtained active ingredient compounds are effective as central nervous system stimulants, disturbance-of-consciousness improving agents and sigma receptor agonists and are used in the form of conventional pharmaceutical preparations. Such preparations are prepared using the conventional fillers, extenders, binding agents, moistening agents, disintegrating agents, surfactants, lubricants, and the like diluents or excipients. These pharmaceutical preparations may have various dosage forms selected according to the purposes of therapy, and typical examples thereof are tablets, pills, powders, solutions, suspensions, emulsions, granules, capsules, suppositories, and injections (solutions, suspensions, etc.). For the manufacture of tablets, a wide variety of carriers so far well known in this field can be used. Thus, use can be made of, for example, vehicles or excipients such as lactose, sucrose, sodium chloride, glucose, urea, starch, calcium carbonate, kaolin, crystalline cellulose and silicic acid, binding agents such as water, ethanol, propanol, simple syrup, glucose solution, starch solution, gelatin solution, carboxymethylcellulose, shellac, methylcellulose, potassium phosphate and polyvinylpyrrolidone, disintegrating agents such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose, disintegration inhibitors such as sucrose, stearin, cacao butter and hydrogenated oils, absorption promoters such as quaternary ammonium bases and sodium lauryl sulfate, wetting agents or humectants such as glycerol and starch, adsorbents such as starch, lactose, kaolin, bentonite and colloidal silica, and lubricants such as refined talc, stearic acid salts, powdered boric acid and polyethylene glycol. When necessary, the tablets may further be provided with a conventional coating to give, for example, sugar-coated tablets, gelatin-coated tablets, enteric-coated tablets, film-coated tablets, or double-coated or multilayer tablets. For the manufacture of pills, a wide variety of carriers well known in the art can be used. Examples are vehicles or excipients such as glucose, lactose, starch, cacao butter, hardened vegetable oils, kaolin and talc, binding agents such as powdered gum arabic, powdered tragacanth gum, gelatin and ethanol, and disintegrating agents such as laminaran and agar. For the manufacture of suppositories, a wide variety of carriers so far known can be used. As examples, there may be mentioned polyethylene glycol, cacao butter, higher alcohols, higher alcohol esters, gelatin and semisynthetic glycerides. Capsules are manufactured in the conventional manner, generally by filling each active ingredient compound in admixture with various carriers such as mentioned above into hard gelatin capsules, soft capsules, etc. In preparing injections, the solutions, emulsions or suspensions are preferably sterilized and are preferably isotonic with blood and, for preparing such dosage forms, all the diluents in conventional use in this field can be employed. Thus, for example, water, ethyl alcohol, macrogol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc. Furthermore, when necessary, the pharmaceutical preparations may contain coloring matters, preservatives, perfumes, flavoring agents, sweetening agents and the like as well as other drugs.

The proportion of the active ingredient compound in these pharmaceutical preparations of this invention is not critical but may suitably be selected in a wide range. Generally, however, the proportion is recommendably selected within the range of about 1 to about 70% by weight, preferably about 5 to about 50% by weight.

The route of administration of these pharmaceutical preparations of this invention is not critical, either, but is selected according to the dosage form, the patient's age, sex and other factors and the severity of the disease to be treated. Thus, for instance, when they are provided in the form of tablets, pills, solutions, suspensions, emulsions, granules or capsules, the preparations are administered orally. Injectable solutions are administered intravenously, either alone or in admixture with conventional fluids for parenteral infusion containing glucose, amino acids and so on. Where necessary, these solutions may also be administered as it is by the intramuscular, intradermal, subcutaneous or intraperitoneal route. Suppositories are administered rectally.

The dosage of these pharmaceutical preparations of the invention may be selected appropriately depending on the method of administration, the patient's age, sex and other factors, severity of the disease and other factors. Generally, however, the daily dose of each active ingredient compound should recommendably be within the range of about 0.0001 to about 50 mg per kilogram of body weight. It is desirable that the active ingredient compound be contained in each unit dosage form in an amount of about 0.001 to about 1,000 mg.

For illustrating the present invention in further detail, some dosage form examples are given below, which are followed by examples illustrating the production of the active ingredient compounds mentioned above and further by test examples using typical active ingredient compounds.

| Dosage Form Example 1 | |
|---|---|
| 5-Methoxy-1-[3-[4-(3-chlorophenyl)-1-piperazinyl]propyl]-3,4-dihydrocarbostyril | 150 g |
| Avicel (trade name, product of Asahi Chemical Industry) | 40 g |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Ethanol | 40 g |

The active ingredient compound of this invention, Avicel, corn starch and magnesium stearate are combined and ground together and the resulting mixture is tableted using a sugar coat R10 mm punch. The tablets obtained are coated with a film coating composition composed of hydroxypropylmethylcellulose, polyethylene glycol 6000, castor oil and ethanol to give film-coated tablets.

| Dosage Form Example 2 | |
|---|---|
| 5-Methoxy-1-[3-[4-(3-trifluoromethylphenyl)-1-piperazinyl]propyl]-3,4-dihydrocarbostyril | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active ingredient compound of this invention, citric acid, lactose, dicalcium phosphate, Pluronic F-68 and sodium lauryl sulfate are admixed.

After size selection using a No. 60 screen, the mixture was granulated by the wet process using an alcoholic solution containing polyvinylpyrrolidone, Carbowax 1500 and Carbowax 6000. When necessary, alcohol is added to make the powder into a paste-like mass. Then, corn starch is added and the blending is continued until uniform granules are formed. The mixture is then passed through a No. 10 screen, placed in a tray and dried in an oven maintained at 100° C. for 12 to 14 hours. The dried granules are sieved through a No. 16 screen, dry sodium lauryl sulfate and dry magnesium stearate are added and, after blending, the mixture is compressed to a desired size and shape using a tableting machine.

The above cores are treated with a varnish and dusted with talc for preventing absorption of moisture and then provided with an undercoat layer. Varnish coating is repeated as many times as sufficient for internal use. The tablets are rendered completely round and smooth by application of a further undercoat layer and a smooth coating. Coloring coating is conducted until a desired coloring is obtained. After drying, the coated tablets are polished to give uniformly polished tablets.

| Dosage Form Example 3 | |
|---|---|
| 5-Chloro-1-[3-[4-(3-methoxyphenyl)-1-piperazinyl]propyl]-3,4-dihydrocarbostyril | 5 g |
| Polyethylene glycol (molecular weight: 4,000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The above parabens, sodium metabisulfite and sodium chloride are dissolved in about half the above-specified volume of distilled water at 80° C. with stirring. The solution obtained is cooled to 40° C., the active ingredient compound of the invention is dissolved in said solution and then polyethylene glycol and polyoxyethylene sorbitan monooleate are dissolved therein. Then, the remaining portion of distilled water for injection is added to the solution to make the final volume and the resulting solution is sterilized by bacterial filtration using an appropriate filter paper to give an injectable solution.

REFERENCE EXAMPLE 1

To a solution of 5-methoxy-3,4-dihydrocarbostyril (53.1 g, 0.3 mole) in 200 ml of dimethylformamide (DMF) was added portionwise 60% sodium hydride in oil (19.2.g, 0.4 mole) at room temperature, and the mixture was stirred for 30 minutes. To the thus-obtained solution of the sodium salt of 5-methoxy-3,4-dihydrocarbostyril in DMF was added 1-bromo-3-chloropropane (94 ml, 0.6 mole). The mixture was stirred at 80°–90° C. for 8 hours. The DMF was distilled off under reduced pressure, and the residue was extracted with chloroform. The extract was washed with water and dried (anhydrous magnesium sulfate), the chloroform was distilled off under reduced pressure, and the residue was recrystallized from ethanol to give 59 g of 1-(3-chloropropyl)-5-methoxy-3,4-dihydrocarbostyril as colorless needles.

Melting point 103°–105° C. $^1$H-NMR (CDCl$_3$, δ ppm): 2.09–2.28 (2H, m), 2.57–2.62 (2H, m), 2.90 (2H, t, J=7.5 Hz), 3.47 (1H, t, J=7.5 Hz), 3.62 (1H, t, J=7.5 Hz), 3.85 (3H, s), 4.05–4.12 (2H, m), 6.64 (1H, d, J=9 Hz), 6.72 (1H, d, J=9 Hz), 7.22 (1H, t, J=9 Hz)

REFERENCE EXAMPLE 2

In the same manner as in Reference Example 1, 60% sodium hydride in oil was added portionwise to a solution of 5-chloro-3,4-dihydrocarbostyril in DMF, the resultant mixture was stirred for 30 minutes, 1-bromo-3-chloropropane was then added, and the resultant mixture was further stirred at 80°–90° C. for 8 hours. The DMF was distilled off under reduced pressure, and the residue was extracted with chloroform. The extract was washed with water and dried (anhydrous magnesium sulfate), the chloroform was distilled off under reduced pressure, and the residue was purified by silica gel column chromatography to give 5-chloro-1-(3-chloropropyl)-3,4-dihydrocarbostyril as a pale yellow oil.

$^1$H-NMR (CDCl$_3$, δppm); 2.15–2.25 (2H, m), 2.65 (2H, t, J=7.5 Hz), 3.04 (2H, t, J=7.5 Hz), 3.48 (2H, t, J=7.5 Hz), 4.08 (2H, t, J=7.5 Hz), 6.99 (1H, d, J=9 Hz), 7.10 (1H, d, J=9 Hz), 7.20 (1H, t, J=9 Hz)

The procedure of Reference Example 1 was followed using appropriate starting materials to give the compounds of Reference Examples 3 to 10 as specified below.

REFERENCE EXAMPLE 3

1-(3-Chloropropyl)-5-ethoxy-3,4-dihydrocarbostyril, colorless oil.

$^1$H-NMR (CDCl$_3$, δppm); 1.42 (3H, t, J=7.5 Hz), 2.08–2.28 (2H, m), 2.57–2.65 (2H, m), 2.91 (2H, t, J=7.5 Hz), 3.42 (1H, t, J=7.5 Hz), 3.62 (1H, t, J=7.5 Hz), 4.01–4.11 (4H, m), 6.62 (1H, d, J=9 Hz), 6.71 (1H, d, J=9 Hz), 7.20 (1H, t, J=9 Hz)

REFERENCE EXAMPLE 4

1-(3-Chloropropyl)-5-isopropoxy-3,4-dihydrocarbostyril, colorless oil.

$^1$H-NMR (CDCl$_3$, δppm); 1.34 (6H, d, J=7.5 Hz), 2.01–2.29 (2H, m), 2.58–2.62 (2H, m), 2.89 (2H, t, J=7.5 Hz), 3.48 (1H, t, J=7.5 Hz), 3.63 (1H, t, J=7.5 Hz), 4.08 (2H, t, J=7.5 Hz), 4.50–4.60 (1H, m), 6.65 (1H, d, J=9 Hz), 6.69 (1H, d, J=9 Hz), 7.18 (1H, t, J=9 Hz)

REFERENCE EXAMPLE 5

1-(3-Chloropropyl)-5-methyl-3,4-dihydrocarbostyril, colorless oil.

$^1$H-NMR (CDCl$_3$, δppm); 2.15–2.25 (2H, m), 2.30 (3H, s), 2.62 (2H, t, J=7.5 Hz), 2.84 (2H, t, J=7.5 Hz), 3.47 (2H, t, J=7.5 Hz), 4.08 (2H, t, J=7.5 Hz), 6.90 (1H, d, J=9 Hz), 6.94 (1H, d, J=9 Hz), 7.16 (1H, t, J=9 Hz)

REFERENCE EXAMPLE 6

1-(3-Chloropropyl)-5-methylthio-3,4-dihydrocarbostyril, yellow oil.

$^1$H-NMR (CDCl$_3$, δppm); 2.09–2.25 (2H, m), 2.47 (3H, s), 2.59–2.70 (2H, 2.91–2.99 (2H, m), 3.36 (1H, t, J=7.5 Hz), 3.47 (1H, t, J=7.5 Hz), 4.08 (2H, t, J=7.5 Hz), 6.90 (1H, d, J=9 Hz), 6.94 (1H, d, J=9 Hz), 7.24 (1H, t, J=9 Hz)

REFERENCE EXAMPLE 7

1-(3-Chloropropyl)-8-methoxy-3,4-dihydrocarbostyril, colorless oil.

$^1$H-NMR (CDCl$_3$, δppm); 2.10–2.30 (2H, m), 2.55–2.65 (2H, m), 2.70–2.80 (2H, m), 3.55 (2H, t, J=7.5 Hz), 3.85 (3H, t, J=7.5 Hz), 4.05 (2H, t, J=7.5 Hz), 6.80 (1H, d, J=9 Hz), 6.90. (1H, d, J=9 Hz), 7.05 (1H, t, J=9 Hz)

REFERENCE EXAMPLE 8

1-(3-Chloropropyl)-5,6-dichloro-3,4-dihydrocarbostyril, colorless oil.

$^1$H-NMR (CDCl$_3$, δppm); 2.10–2.25 (2H, m), 2.64–2.70 (2H, m), 3.08–3.15 (2H, m), 3.47 (2H, t, J=7.5 Hz), 4.05 (2H, t, J=7.5 Hz), 6.95 (1H, d, J=9 Hz), 7.36 (1H, d, J=9 Hz)

REFERENCE EXAMPLE 9

5-Acetylamino-1-(3-chloropropyl)-3,4-dihydrocarbostyril, colorless oil.

$^1$H-NMR (CDCl$_3$, δppm); 2.10–2.25 (2H, m), 2.15 (3H, s), 2.64–2.70 (2H, m), 3.08–3.15 (2H, m), 3.48 (2H, t, J=7.5 Hz), 4.05 (2H, t, J=7.5 Hz), 6.62 (1H, d, J=7.5 Hz), 6.75 (1H, d, J=9 Hz), 7.25 (1H, t, J=9 Hz)

REFERENCE EXAMPLE 10

1-(3-Chloropropyl)-5-methoxycarbostyril, colorless oil.

$^1$H-NMR (CDCl$_3$, δppm); 2.15–2.38 (2H, m), 3.55 (2H, t, J=7.5 Hz), 3.96 (3H, s), 4.42 (2H, t, J=7.5 Hz), 6.62 (1H, d, J=10 Hz), 6.65 (1H, d, J=9 Hz), 7.05 (1H, t, J=9 Hz), 7.50 (1H, t, J=9 Hz), 8.15 (1H, d, J=10 Hz)

EXAMPLE 1

A solution composed of 1-(3-chloropropyl)-5-methoxy-3,4-dihydrocarbostyril (39.1 g, 0.15 mole), sodium iodide (33.5 g, 0.23 mole) and acetonitrile (200 ml) was heated under reflux for 1 hour and then cooled to room temperature. To this solution was further added 1-(3-chlorophenyl) piperazine (39.3 g, 0.2 mole) and sodium corbonate (21 g, 0,2 mole). The mixture was further stirred for 4 hours and then filtered while it was hot. The filtrate was concentrated under reduced pressure. The residue was purified by silica gel column chromatography, made acidic with hydrochloric acid and then recrystallized from ethanol to give 31.2 g of 1-[3-[4-(3-chlorophenyl)-1-piperazinyl]propyl]-5-methoxy-3,4-dihydrocarbostyril hydrochloride as colorless flakes.

Melting point 239°–242° C. (decomposition).

EXAMPLE 2 TO 56

The procedure of Example 1 was followed using appropriate starting materials to give the compounds listed below in Table 1. In Table 1, the solvent means a solvent for recrystallization.

TABLE 1
| Example | Structure | Crystal Form (solvent) | mp (°C.) |
|---------|-----------|------------------------|----------|
| 2 | 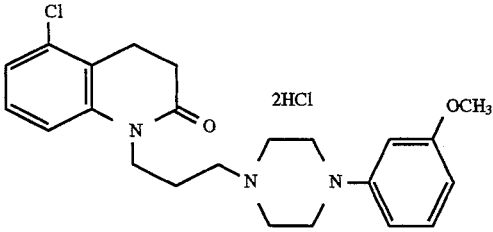 | colorless needles (methanol) | 212–213 (dec.) |
| 3 | 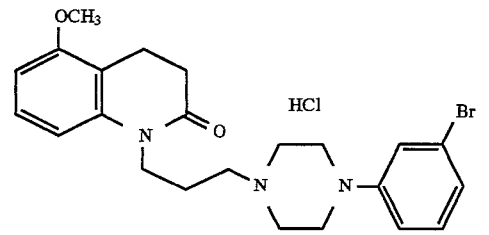 | colorless needles (ethanol) | 228–231 (dec.) |
| 4 | 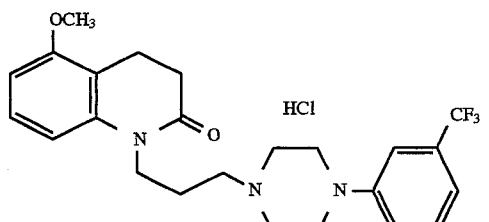 | colorless needles (ethanol) | 207–208 |
| 5 | 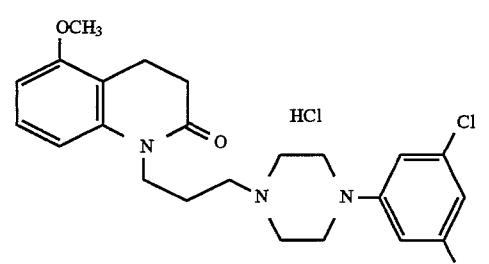 | white powder (ethanol) | 226–228 (dec.) |
| 6 | 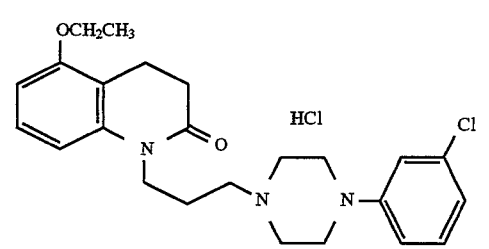 | white powder (ethanol) | 226–228 (dec.) |
| 7 | 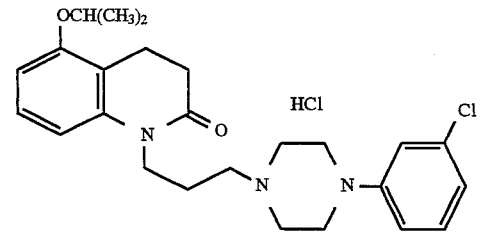 | colorless flakes (ethanol) | 218–229 (dec.) |

TABLE 1-continued
| Example | Structure | Crystal Form (solvent) | mp (°C.) |
|---|---|---|---|
| 8 | 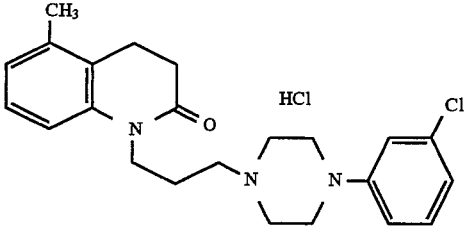 | colorless needles (ethanol) | 196–198 |
| 9 | 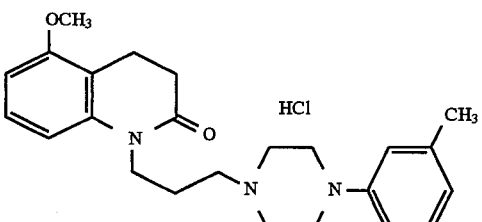 | colorless needles (ethanol) | 220–228 (dec.) |
| 10 | 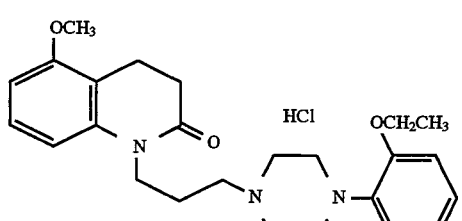 | colorless needles (ethanol) | 168–173 (dec.) |
| 11 | 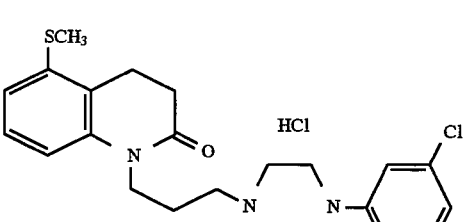 | colorless needles (ethanol) | 221–224 (dec.) |
| 12 | 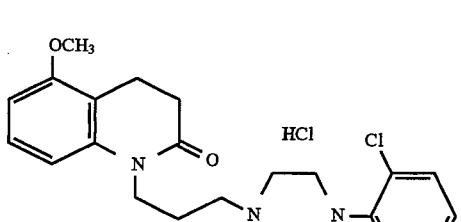 | colorless needles (ethanol) | 214–215 (dec.) |
| 13 | 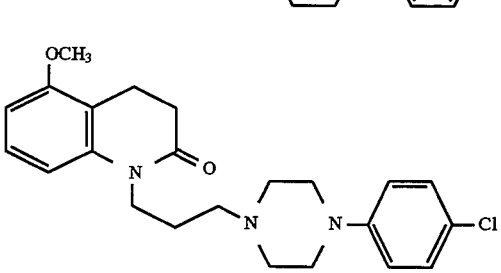 | colorless needles (ethanol) | 124–125 |

TABLE 1-continued
| Example | Structure | Crystal Form (solvent) | mp (°C.) |
|---|---|---|---|
| 14 | 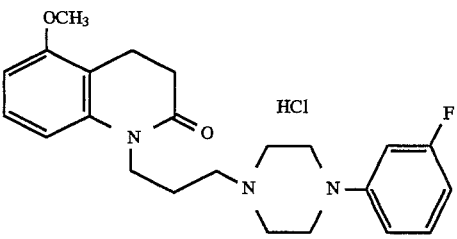 | colorless needles (ethanol) | 236–240 (dec.) |
| 15 | 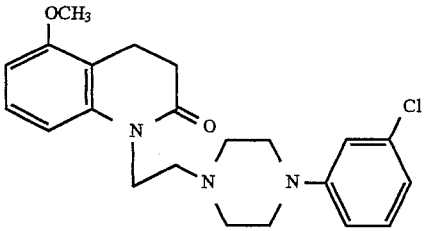 | colorless needles (ethanol) | 132–132.5 |
| 16 | 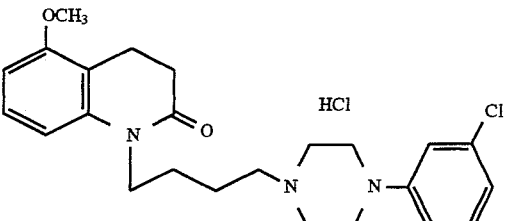 | colorless needles (ethanol) | 128–129 (dec.) |
| 17 | 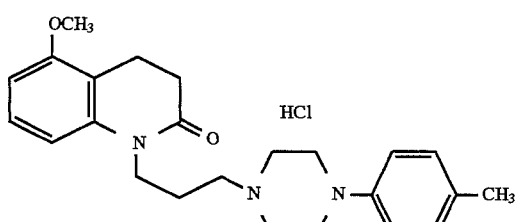 | colorless needles (ethanol) | 226–229 (dec.) |
| 18 | 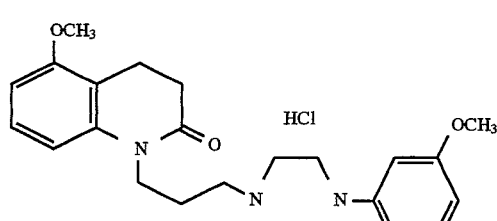 | colorless needles (ethanol) | 176–177 |
| 19 | 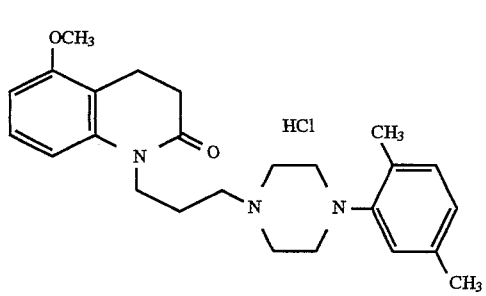 | colorless needles (ethanol) | 223–226 (dec.) |

TABLE 1-continued
| Example | Structure | Crystal Form (solvent) | mp (°C.) |
|---|---|---|---|
| 20 | 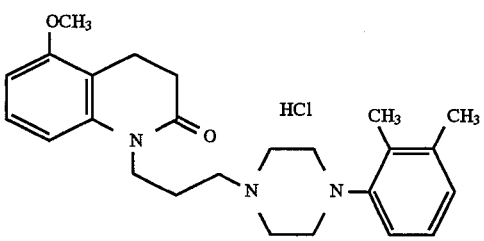 | colorless needles (ethanol) | 228–230 (dec.) |
| 21 | 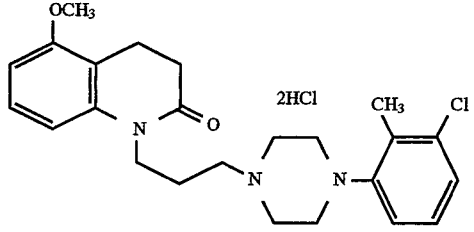 | colorless needles (ethanol) | 232–234 (dec.) |
| 22 | 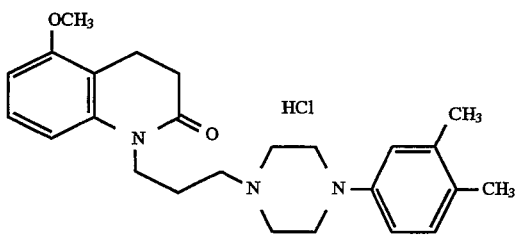 | colorless needles (ethanol) | 212–216 |
| 23 | 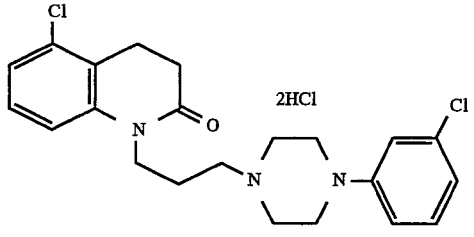 | colorless needles (ethanol) | 217–218 (dec.) |
| 24 | 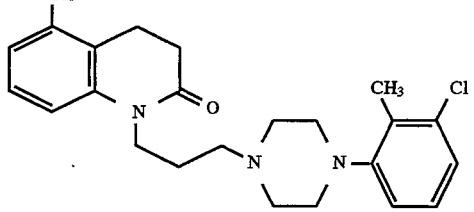 | colorless prisms (ethanol) | 185.5–186.5 |
| 25 | 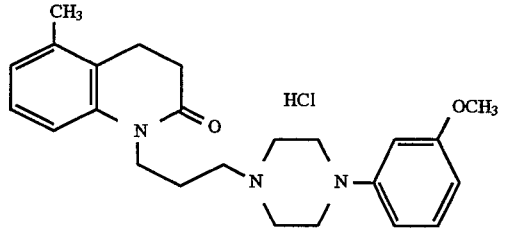 | colorless needles (ethanol) | 145–146 |

TABLE 1-continued

| Example | Structure | Crystal Form (solvent) | mp (°C.) |
|---|---|---|---|
| 26 | CH3O- quinolinone with propyl-piperazine-(3-chlorophenyl) | white powder (ethanol) | 159–161 |
| 27 | CH3O- quinolinone with propyl-piperazine-(3-chlorophenyl), HCl | colorless needles (ethanol) | 224–229 (dec.) |
| 28 | CH3- quinolinone with propyl-piperazine-(3-chlorophenyl), HCl | white powder (ethanol) | 136–137 |
| 29 | OCH2CH=CH2 quinolinone with propyl-piperazine-(3-chlorophenyl), HCl | colorless needles (ethanol) | 180–185 |
| 30 | Cl-quinolinone with propyl-piperazine-(3-chlorophenyl), HCl | colorless needles (ethanol) | 172–173 |
| 31 | Cl-quinolinone with propyl-piperazine-(3-methoxyphenyl), HCl | colorless needles (ethanol) | 185–187 |
| 32 | OH-quinolinone with propyl-piperazine-(3-chlorophenyl) | colorless prisms (ethanol) | 200–201.5 (dec.) |

TABLE 1-continued

| Example | Structure | Crystal Form (solvent) | mp (°C.) |
|---|---|---|---|
| 33 | 5-Cl-quinolinone-N-(CH₂)₃-piperazine-(3-NO₂-phenyl) · HCl | yellow needles (ethanol) | 204–211 (dec.) |
| 34 | 5-Cl-quinolinone-N-(CH₂)₃-piperazine-(3-NH₂-phenyl) | colorless needles (ethanol) | 161–163 |
| 35 | 5-Cl-quinolinone-N-(CH₂)₃-piperazine-(3-NHCOCH₃-phenyl) · HCl | colorless needles (ethanol) | 177–178 |
| 36 | 5-Cl-quinolinone-N-(CH₂)₃-piperazine-(3-OH-phenyl) | colorless granulars (dimethyl-formamide-methanol) | 236–239 |
| 37 | 5-Cl-quinolinone-N-(CH₂)₃-piperazine-(3-O-(CH₂)₂CH₃-phenyl) · HCl | colorless granulars (ethanol) | 186–188 |
| 38 | 5-Cl-quinolinone-N-(CH₂)₃-piperazine-(3-OCH₂-phenyl-phenyl) · HCl | colorless granulars (ethanol) | 181–183 |

TABLE 1-continued

| Example | Structure | Crystal Form (solvent) | mp (°C.) |
|---|---|---|---|
| 39 | 5-OCH₃ quinolin-2(1H)-one, 1-[3-[4-(3-chlorophenyl)piperazin-1-yl]propyl]-, HCl | colorless needles (ethanol) | 232–236 (dec.) |
| 40 | 5-OCH₃ quinolin-2(1H)-one, 1-[3-[4-(3-bromophenyl)piperazin-1-yl]propyl]-, HCl | colorless needles (ethanol) | 222–232 (dec.) |
| 41 | 5-OCH₃ quinolin-2(1H)-one, 1-[3-[4-(3-trifluoromethylphenyl)piperazin-1-yl]propyl]-, HCl | colorless granulars (ethanol) | 221–228 (dec.) |
| 42 | 8-OCH₃ 3,4-dihydroquinolin-2(1H)-one, 1-[3-[4-(3-chlorophenyl)piperazin-1-yl]propyl]-, HCl | white powder (ethanol) | 196–201 |
| 43 | 5-NHCOCH₃ 3,4-dihydroquinolin-2(1H)-one, 1-[3-[4-(3-chlorophenyl)piperazin-1-yl]propyl]-, HCl | colorless granulars (ethanol) | 177–183 (dec.) |
| 44 | 5-NH₂ 3,4-dihydroquinolin-2(1H)-one, 1-[3-[4-(3-chlorophenyl)piperazin-1-yl]propyl]-, 2HCl | white powder (ethanol) | 218–240 (dec.) |

TABLE 1-continued

| Example | Structure | Crystal Form (solvent) | mp (°C.) |
|---|---|---|---|
| 45 | 3,4-dichlorophenyl-CH2CH2-C(=O)-N(quinolinone)-(CH2)3-piperazine-N-(3-methoxyphenyl) · HCl | colorless flakes (ethanol) | 212–216 |
| 46 | 5-methoxy-3,4-dihydroquinolin-2(1H)-one-N-(CH2)3-piperazine-N-(2,5-dichlorophenyl) · HCl | white powder (ethanol) | 215–221 (dec.) |
| 47 | 5-methoxy-3,4-dihydroquinolin-2(1H)-one-N-(CH2)3-piperazine-N-(3,4-dichlorophenyl) · HCl | white powder (ethanol) | 228–234 |
| 48 | 5-methoxy-3,4-dihydroquinolin-2(1H)-one-N-(CH2)3-piperazine-N-(3-nitrophenyl) · 2HCl | colorless flakes (ethanol) | 221–222 (dec.) |
| 49 | 5-methoxy-3,4-dihydroquinolin-2(1H)-one-N-(CH2)3-piperazine-N-(3-aminophenyl) | brown granulars (ethanol) | 132–133 |
| 50 | 5-methoxy-3,4-dihydroquinolin-2(1H)-one-N-(CH2)3-piperazine-N-(3-acetamidophenyl) · 2HCl | pale yellow powder (ethanol) | 198–201 |

TABLE 1-continued

| Example | Structure | Crystal Form (solvent) | mp (°C.) |
|---|---|---|---|
| 51 | (5-OCH₃ 3,4-dihydrocarbostyril)-N-(CH₂)₃-piperazine-N'-(3-hydroxyphenyl) · HCl | white powder (ethanol) | 205–208 (dec.) |
| 52 | (5-OCH₃ 3,4-dihydrocarbostyril)-N-(CH₂)₃-piperazine-N'-(3-butoxyphenyl) · 2HCl | white powder (ethanol) | 176–179 |
| 53 | (5-OCH₃ 3,4-dihydrocarbostyril)-N-(CH₂)₃-piperazine-N'-(3-isopropoxyphenyl) · 2HCl | white powder (ethanol) | 170–173 |
| 54 | (5-OCH₃ 3,4-dihydrocarbostyril)-N-(CH₂)₃-piperazine-N'-(3-benzyloxyphenyl) · HCl | white powder (ethanol) | 184–186 (dec.) |
| 55 | (5-OCH₃ 3,4-dihydrocarbostyril)-N-(CH₂)₃-piperazine-N'-(3-cyanophenyl) · HCl | colorless flakes (ethanol) | 235–236 |
| 56 | (5-OCH₃ 3,4-dihydrocarbostyril)-N-(CH₂)₃-piperazine-N'-phenyl · HCl | colorless flakes (ethanol) | 240–243 (dec.) |

EXAMPLE 57

5-Chloro-1-[3-[4-(3-nitrophenyl)-1-piperazinyl]-propyl]-3,4-dihydrocarbostyril (3 g) was dissolved in 100 ml of ethanol, 2 ml of concentrated hydrochloric acid was added, and catalytic reduction was carried out at 3 atmospheres in the presence of 1.5 g of 5% palladium-carbon. The catalyst was then filtered off, the filtrate was concentrated under reduced pressure, and the residue was recrystallized from ethanol to give 2.5 g of 1-[3-[4-(3-aminophenyl)-1-piperazinyl]propyl]-5-chloro-3,4-dihydrocarbostyril as colorless needles.

Melting point 161°–163° C.

EXAMPLE 58

1-[3-[4-(3-aminophenyl)-1-piperazinyl]propyl]-5-chloro-3,4-dihydrocarbostyril (1 g) was dissolved in 10 ml of chloroform, 5 ml of acetic anhydride and 0.1 g of 4-dimethylaminopyridine were added, and the mixture was heated under reflux for 30 minutes. The reaction mixture was concentrated under reduced pressure, and the residue was purified by silica gel column chromatography and then converted to the hydrochloride form, which was recrystallized from ethanol to give 900 mg of 1-[3-[4-(3-acetylaminophenyl)-1-piperazinyl]propyl]-5-chloro-3,4-dihydrocarbostyril hydrochloride as colorless needles.

Melting point 177°–178° C.

EXAMPLE 59

5-Acetylamino-1-[3-[4-(3-chlorophenyl)-1-piperaznyl]propyl]-3,4-dihydrocarbostyril (800 mg) was dissolved in 20 ml of 6N hydrochloric acid, and the mixture was heated under reflux for 1 hour. The reaction mixture was concentrated under reduced pressure and the residue was recrystallized from ethanol to give 480 mg of 5-amino-1-[3-[4-(3-chlorophenyl)-1-piperazinyl]propyl]-3,4-dihydrocarbostyril dihydrochloride as a white powder.

Melting point 218°–240° C. (decomposition).

EXAMPLE 60

The compound of Example 49 was produced by following the procedure of Example 57 using the corresponding starting material.

EXAMPLE 61

The compounds of Example 43 and Example 50 were produced by following the procedure of Example 58 using the corresponding starting materials.

EXAMPLE 62

The compounds of Example 44 and Example 49 were produced by following the procedure of Example 59 using the corresponding starting materials.

Pharmacological test 1

Acceleration of recovery from halothane anesthesia (recovery accelerating effect)

The test was performed using mice according to the method described in the British Journal of Pharmacology, 58, 27–35 (1976). Thus, 4- to 5-week-old male mice (weighting 20–29 g), fasted for 18–20 hours, were placed in a chamber supplied with air containing 4% halothane at a rate of 2 L/min. The mice immediately lost righting reflex in the chamber. Even after they were taken out from the chamber, the mice continued to show loss of righting reflex for a while and, then, regained the reflex. The time from loss of righting reflex to recovery of the reflex was measured and used as the duration of halothane-induced anesthesia. The test drug, either suspended or dissolved in a 5% saline solution of gum arabic was administered orally one hour before anesthesia loading. The control mice received 5% gum arabic in saline. The recovery accelerating effect of the test drug was expressed in the ratio of the duration of adnesthesia in the mice given the test drug to that in the control mice (% of control). The results are shown in Table 2.

TABLE 2

| Test compound | Route of administration and dose (mg/kg) | | Duration of halothane-induced anesthesia (% control) |
|---|---|---|---|
| Compound of Ex. 1 | Oral | 100 | 52 |
| Compound of Ex. 2 | Oral | 100 | 51 |
| Compound of Ex. 3 | Oral | 100 | 54 |
| Compound of Ex. 4 | Oral | 100 | 66 |
| Compound of Ex. 5 | Oral | 100 | 85 |
| Compound of Ex. 6 | Oral | 100 | 68 |
| Compound of Ex. 7 | Oral | 100 | 86 |
| Compound of Ex. 8 | Oral | 100 | 74 |
| Compound of Ex. 32 | Oral | 100 | 88 |
| Compound of Ex. 35 | Oral | 30 | 85 |
| Compound of Ex. 36 | Oral | 30 | 65 |
| Compound of Ex. 38 | Oral | 30 | 86 |
| Compound of Ex. 48 | Oral | 100 | 61 |
| Compound of Ex. 55 | Oral | 30 | 83 |

In Table 2, the duration of anesthesia in mice treated with each test compound is shown with the duration of halothane-induced anesthesia in the control mice being taken as 100%. The compounds of this invention were found to shorten the duration of anesthesia, as shown in Table 2, indicating that they had central nervous system stimulant activity.

Pharmacological test 2

Evaluation of disturbance-of-consciousness improving effect in a mouse model of coma following head injury.

The test was conducted according to the method described in the Journal of Japan Accident Medical Association, 25, 202 (1977) and Igaku no Ayumi, 102, 867–869 (1977). Thus, 4- to 5-week-old male mice (weighting 20–29 g) were fasted for 18–20 hours. Then, the head of each mouse was fixed on a polystyrene foam pillow and a shock was given to the parietal region by dropping a cylindrical acrylic resin rod through a clear plastic tube. Observation of impaired consciousness was made in regard to the following two terms: the time from the onset of coma following the shock to recovery of righting reflex (RR time) and the time to recovery of spontaneous mobility (SM time). Each test compound, either suspended or dissolved in a 5% solution of gum arabic solution in physiological saline, was administered orally one hour before anesthesia loading. Control mice received 5% gum arabic in saline. The disturbance-of-consciousness improving effect of the test compound was expressed in the ratio of the RR or SM time for the mice treated with the test compound to the RR or SM time for the control mice (% of control). The results are shown in Table 3.

TABLE 3

| Test compound | Route of administration and dose (mg/kg) | | RR time (% of control) | SM time (% of control) |
|---|---|---|---|---|
| Compound of Ex. 1 | Oral | 30 | 20 | 20 |
| Compound of Ex. 2 | Oral | 30 | 28 | 28 |
| Compound of Ex. 4 | Oral | 30 | 36 | 48 |
| Compound of Ex. 41 | Oral | 30 | 51 | 58 |
| Compound of Ex. 48 | Oral | 30 | 52 | 52 |

In Table 3, as an indicator of recovery from the coma caused by head injury, the RR or SM time for mice treated with each test compound is shown in percentage with the RR or SM time for control mice being taken as 100%. The compound of the present invention clearly shortened both the RR time and SM time in this model, indicating that the compound accelerates recovery from the coma caused by head injury and has an ameliorative effect on impaired consciousness.

Pharmacological Test 3

Binding affinity for the sigma receptor

A membrane fraction was prepared and a [$^3$H]-1,3-di[2-tolyl]guanidine (DTG) binding test was performed, both by the method of Wettstein et al. [Wettstein, J. F., Romman, F. J., Rocher, M. N. and Junienr J. L., Psychopharmacology, 104, 157–163 (1991)]. Thus, a Wistar strain male rat was decapitated and the whole brain was excised and homogenized in 30 volumes of ice-cooled 50 mM Tris hydrochloride buffer (pH 7.4). The homogenate was then centrifuged at 4° C. and 50,000 g for 15 minutes. The sediment obtained was suspended in one volume of the same buffer as mentioned above and, after 45 minutes of incubation at 37° C., the suspension was centrifuged again. The sediment obtained was suspended in one volume of the same buffer and the suspension was stored frozen at −80° C. until use.

The binding experiment was performed as follows. The frozen tissue preparation was thawed and centrifuged at 4° C. and 50,000 g for 15 minutes and the sediment obtained was suspended in 10 volumes of 5 mM Tris hydrochloride buffer (pH 7.4). The suspension was used as the membrane preparation. In test tubes were placed varying dilutions of the test compound (50 μl), [$^3$H]-DTG (50 μl, final concentration 3 nM) and the membrane preparation (150 μl) (total volume 250 μl per tube). The reaction began on addition of the membrane preparation. The tubes were incubated at 25° C. for 60 minutes and using a cell harvester (Brandel), the reaction was stopped by suction filtration through a Whatman GF/B filter saturated in advance with 0.5% polyethylenimine and the filter was immediately washed with three 3-ml portions of ice-cooled 5 mM Tris hydrochloride buffer.

The filter was transferred to a vial and after addition of 5 ml of a liquid scintillation cocktail (Aquasol 2), the vial was allowed to stand in the dark for a predetermined time. The radioactivity was then measured using a scintillation counter. The amount of specific binding was determined by subtracting the binding amount in the presence of 10 μM haloperidol from the total binding amount. The IC$_{50}$ values were calculated by computer analysis using the nonlinear least squares method.

The results are shown in Table 4.

TABLE 4

| Test compound | Inhibitory activity IC$_{50}$ (μM ± SED) |
| --- | --- |
| Compound of Example 1 | 0.34 ± 0.11 |
| Compound of Example 2 | 0.13 ± 0.016 |
| Compound of Example 4 | 0.49 ± 0.032 |
| Compound of Example 39 | 0.98 ± 0.13 |
| Compound of Example 41 | 0.82 ± 0.11 |
| Compound of Example 48 | 0.87 ± 0.14 |
| Compound of Example 49 | 1.21 ± 0.14 |
| Compound of Example 53 | 0.49 ± 0.048 |
| Compound of Example 56 | 0.71 ± 0.066 |

What is claimed is:

1. A carbostyril derivative of the general formula

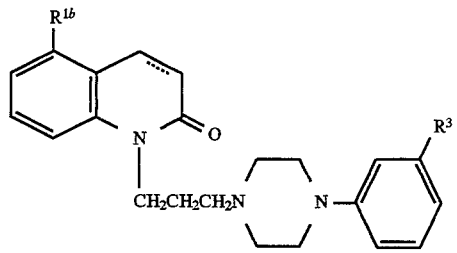

wherein $R^{1b}$ is a methoxy, ethoxy, methyl or chloro group, $R^3$ is a methoxy, chloro, bromo, nitro, or trifluoromethyl group, and the carbon-carbon bond between the positions 3 and 4 of the carbostyril skeleton is a single bond or a double bond, or a salt thereof.

2. 5-Methoxy-1-[3-[4-(3-chlorophenyl)-1-piperazinyl]propyl]-3,4-dihydrocarbostyril.

3. 5-Methoxy-1-[3-[4-(3-bromophenyl)-1-piperazinyl]propyl]-3,4-dihydrocarbostyril.

4. 5-Methoxy-1-[3-[4-(3-nitrophenyl)-1-piperazinyl]propyl]-3,4-dihydrocarbostyril.

5. 5-Ethoxy-1-[3-[4-(3-chlorophenyl)-1-piperazinyl]propyl]-3,4-dihydrocarbostyril.

6. 5-Chloro-1-[3-[4-(3-methoxyphenyl)-1-piperazinyl]propyl]-3,4-dihydrocarbostyril.

7. The carbostyril derivative or a salt thereof as claimed in claim 1 wherein $R^{1b}$ is a methoxy or ethoxy group, and $R^3$ is a chloro, bromo, nitro or trifluoromethyl group.

8. The carbostyril derivative or a salt thereof as claimed in claim 1 wherein $R^{1b}$ is a chloro group and $R^3$ is a methoxy.

9. The carbostyril derivative or a salt thereof as claimed in claim 1 wherein the carbon-carbon bond between the positions 3 and 4 of the carbostyril skeleton is a single bond.

10. The carbostyril derivative or a salt thereof as claimed in claim 1 wherein the carbon-carbon bond between the positions 3 and 4 of the carbostyril skeleton is a double bond.

11. A pharmaceutical composition useful as a consciousness-inducing agent comprising a consciousness-inducing effective amount of a carbostyril compound or a pharmaceutically acceptable salt thereof as claimed in claim 1 as an active ingredient and a pharmaceutically acceptable carrier.

12. A pharmaceutical composition useful as a central nervous system stimulant comprising a central nervous system stimulant effective amount of a carbostyril compound or a pharmaceutically acceptable salt thereof as claimed in claim 1 as an active ingredient and a pharmaceutically acceptable carrier.

13. A pharmaceutically composition useful as a sigma receptor agonist comprising a carbostyril compound or a pharmaceutically acceptable salt thereof as claimed in claim 1 as an active ingredient in an amount of 0.001 to 1000 mg per unit dosage form, and a pharmaceutically acceptable carrier.

* * * * *